US006794135B1

(12) United States Patent
Kopreski et al.

(10) Patent No.: US 6,794,135 B1
(45) Date of Patent: Sep. 21, 2004

(54) METHOD FOR DETECTION OF 5T4 RNA IN PLASMA OR SERUM

(75) Inventors: Michael S. Kopreski, Long Valley, NJ (US); Christopher D. Gocke, Ellicott City, MD (US)

(73) Assignee: Oncomedx, Inc., Hackettstown, NJ (US)

( * ) Notice: Subject to any disclaimer, the term of this patent is extended or adjusted under 35 U.S.C. 154(b) by 0 days.

(21) Appl. No.: 09/649,371

(22) Filed: Aug. 28, 2000

Related U.S. Application Data

(63) Continuation-in-part of application No. 09/155,152, filed as application No. PCT/US97/03479 on Mar. 14, 1997, now Pat. No. 6,329,179.
(60) Provisional application No. 60/014,730, filed on Mar. 26, 1996.

(51) Int. Cl.$^7$ ............................ C12P 19/34; C12Q 1/68; G01N 33/00; C07H 21/02; C07H 21/04
(52) U.S. Cl. .............................. 435/6; 435/6; 435/91.1; 435/91.51; 436/94; 536/23.1; 536/24.3; 536/24.33
(58) Field of Search .......................... 435/6, 91.1, 91.2, 435/91.51, 183; 436/94; 536/23.1, 24.3, 24.33, 25.3

(56) References Cited

U.S. PATENT DOCUMENTS

| 5,576,178 A | * 11/1996 | Emanuel et al. ................ 435/6 |
| 5,869,053 A | 2/1999 | Stern et al. |
| 6,329,179 B1 | * 12/2001 | Kopreski .................... 435/91.2 |

FOREIGN PATENT DOCUMENTS

| EP | 0 336 582 A | 10/1989 |
| WO | WO 97 35589 A | 10/1997 |

OTHER PUBLICATIONS

Southall et al., Immunohistological distribution of 5T4 antigen in normal and malignant tissue, Br. J. Cancer, 61, 89–95, 1990.*
Kopreski et al., Sensitive detection of tumor messenger RNA in the serum of patients with malignant melanoma. Clin. Cancer Res., 5, 1961–1965, Aug. 1999.*
Myers et al., Isolation of a cDNA encoding 5T4 oncofetal trophoblast glycoprotein. J. Biol. Chem. 269, 9319–9324, 1994.*
Datta et al., Sensitive detection of occult breast cancer by the reverse–transcriptase polymerase chain reaction. J. Clin. Oncology 12, 475–482, 1994.*
Myers et al., Isolation of a cDNA encoding 5T4 oncofetal trophoblast glycoprotein. J. Biol. Chem. 269, 9319–9324, 1994.*
Wieczorek et al., Diagnostic and prognostic value of RNA–Proteolipid in sera of patients with malignant disorders following therapy: first clinical evaluation of a novel tumor marker. Cancer Res. 47, 6407–6412, 1987.*
King et al., organization of the mouse and human 5T4 oncofoetal leucine–rich glycoprotein genes and expression in foetal and adult murine tissues. Biochim. Biophys. Acta, 1445, 257–270, Jun. 1999.*
Southall et al., Immunohistological distribution of 5T4 antigen in normal and malignant tissue. Br. J. Cancer, 61, 89–95, 1990.*
Kopreski et al., Detection of tumor messenger RNA in the serum of patients with malignant melanoma. Clin. Cancer Res. 5, 1961–1965, Aug. 1999 (This is applicant's publication).*
Kopreski et al., "Circulating RNA as a tumor marker", Clinical Chemistry, vol. 47, No. 2, p. 362, Feb. 2001.
King et al., "Organization of the mouse and human 5T oncofoetal leucine–rich glycoprotein genes and expression in foetal and adult murine tissues", Biochimica et Biophysica Acta. Gene Structure and Expression, Elsevier, Amsterdam, NL, vol. 1445, No. 3, Jun. 9, 1999, pp. 257–270.
Jour. of Biological Chemistry, vol. 269, No. 12, pp. 9319–9324.
American Journal of Pathology, vol. 138, No. 2, Feb. 1991.
Br. J. Cancer (1990) 61, 96–100.
Br. J. Cancer (1992) 66, 867–869.
Br. J. Cancer (1994) 69, 899–902.
Br. J. Cancer (1990) 61, 89–95.
Br. J. Cancer (1988), 57, 239–246.
Int. J. Cancer 45, 179–184 (1990).
Biochemica et Biophysica Acta 1445 (1999) 257–270.
Clinical Cancer Research vol. 3, 1923–1930, Nov. 1997.
Pfleiderer et al., "Detection of Tumor Cells in Peripheral Blood and Bone marrow from Ewing Tumour Patients by Rt–PCR," *Int. J. Caner (Red. Oncol.)* 1995, 64: 135–139.
Komeda et al., "Sensitive Detection of Circulating Hepatocellular Carcinoma Cells in Peripheral Venous Blood", *Cancer* 1995, 75: 2214–2219.
Kopreski et al., "Detection of Tumor Messenger RNA in the Serum of Patients with Malignant Melanoma", *Clinical Cancer Research* Aug. 1999, 5: 1961–1965.
Hasselmann et al., "Detection of Tumor–Associated circulating mRNA in serum, plasma and blood cells from patients with disseminated malignant melanoma," *Oncology Reports*, 2001, 8:115–118.

* cited by examiner

Primary Examiner—Ethan Whisenant
Assistant Examiner—Frank Lu

(57) ABSTRACT

This invention relates to methods of detecting or inferring the presence of malignant or premalignant cells in a human that express 5T4. Provided are methods for detecting 5T4 RNA in blood, plasma, serum, other bodily fluids, cells, and tissues. The invention thereby provides an aid for the detection, diagnosis, monitoring, treatment, or evaluation of neoplastic disease.

23 Claims, No Drawings

SEQUENCE LISTING

<160> NUMBER OF SEQ ID NOS: 3

<210> SEQ ID NO 1
<211> LENGTH: 18
<212> TYPE: DNA
<213> ORGANISM: Homo sapiens

```
<400> SEQUENCE: 1
tcttcgcctc ttgttggc                                                 18

<210> SEQ ID NO 2
<211> LENGTH: 17
<212> TYPE: DNA
<213> ORGANISM: Homo sapiens

<400> SEQUENCE: 2
tgcaggaagg aacggga                                                  17

<210> SEQ ID NO 3
<211> LENGTH: 20
<212> TYPE: DNA
<213> ORGANISM: Homo sapiens

<400> SEQUENCE: 3
ttggtaggga aggaattggg                                               20
```

METHOD FOR DETECTION OF 5T4 RNA IN PLASMA OR SERUM

This application is a continuation-part of U.S. patent application, Ser. No. 09/155,152, filed Sep. 22, 1998, now U.S. Pat. No. 6,329,179B1 which is the national stage of PCT/U.S.97/03479, filed Mar. 14, 1997 the entire disclosure of which is hereby incorporated by reference, which claims the benefit of the filing date of Provisional U.S. patent application, Ser. No. 60/014,730, filed Mar. 26, 1996, the entire disclosure of which is hereby incorporated by reference.

BACKGROUND OF THE INVENTION

This invention relates to methods for detecting 5T4 RNA in bodily fluids including but not limited to plasma and serum Ribonucleic acid (RNA) is essential to the processes that allow translation of the genetic code to form proteins necessary for cellular functions, both in normal and neoplastic cells. While the genetic code structurally exists as deoxyribonucleic acid (DNA), it is the function of RNA to carry and translate this code to the cellular sites of protein production. The pathogenesis and regulation of cancer is dependent upon RNA-mediated translation of specific genetic codes to produce proteins involved with cell proliferation, regulation, and death, including but not limited to those RNA associated with specific cellular processes characteristic of cancer, such as processes associated with metastatic potential, invasiveness, and alterations of cell-cell interactions. Furthermore, some RNA and their translated proteins, although not necessarily involved in specific neoplastic pathogenesis or regulation, may serve to delineate recognizable characteristics of particular neoplasms by either being elevated or inappropriately expressed. The RNA associated with cancer and premalignant or neoplastic states have been referred to herein as tumor-derived, or tumor-associated RNA. The invention, as described in U.S. patent application Ser. No. 09/155,152, incorporated by reference herein in its entirety, provides a method by which tumor-associated or tumor-derived RNA in bodily fluids such as plasma and serum can be detected and thus utilized for the detection, monitoring, or evaluation of cancer or premalignant conditions.

5T4 is a transmembrane glycoprotein present in trophoblast tissue whose gene structure has recently been characterized (Hole, 1988; Hole, 1990; Myers, 1994; King, 1999). The protein is only expressed at low levels on cells of a few other normal epithelium. Significantly, 5T4 expression is upregulated in the cells of many epithelial cancers and premalignant tissues, including but not limited to those of the breast, ovary, lung, cervix, colorectum, stomach, pancreas, bladder, endometrium, brain, kidney, and esophagus (Jones, 1990; Southall, 1990; Starzynska, 1992; Starzynska, 1994), and its mRNA is thereby a tumor-associated RNA. Overexpression of 5T4 is particularly associated with cancers of high metastatic potential and worse prognosis (Mulder, 1997; Styns; 1994). Detection of 5T4 thereby provides a method for detecting and monitoring a wide spectrum of cancers and premalignancies, and may have prognostic; significance. 5T4 further provides a potential target for cancer therapies, particularly monoclonal antibody-based therapies. 5T4 thus appear an important tumor marker, and a test of blood or other bodily fluids that detects the presence of 5T4 would be useful. However, the 5T4 protein has not been reported to be shed from the cell surface or to circulate in blood.

The present invention describes a method of evaluating for 5T4 by detecting 5T4 mRNA in blood, particularly plasma and serum, and other bodily fluids including but not limited to urine, effusions, ascites, saliva, cerebrospinal fluid, cervical, vaginal, and endometrial secretions, gastrointestinal secretions, bronchial secretions, and associated tissue washings.

SUMMARY OF THE INVENTION

The present invention provides a method for detecting of 5T4 RNA in blood or a blood fraction, including plasma and serum, and other bodily fluids, the method comprising the steps of extracting RNA from blood, plasma, serum, and other bodily fluid, amplifying 5T4 mRNA or its cDNA, and detecting the amplified product of 5T4 mRNA or its cDNA.

In a first aspect, the present invention provides methods for detecting 5T4 RNA in blood or blood fractions, including plasma and serum, in a human as an aid in the detection, diagnosis, monitoring, treatment, or evaluation of neoplastic disease, including early cancer, non-invasive cancer, carcinoma in-situ, premalignancy, invasive cancer; advanced cancer, and benign neoplasm, wherein the method comprises the steps of extracting RNA from blood or blood plasma or serum, amplifying a fraction of the extracted RNA or the corresponding cDNA wherein said fraction comprises 5T4 RNA, and detecting the amplified product of 5T4 RNA or its cDNA.

The invention further provides a method for detecting 5T4 RNA in all bodily fluids including but not limited to whole blood, plasma, serum, urine, effusions, ascitic fluid, saliva, cerebrospinal fluid, cervical secretions, vaginal secretions, endometrial secretions, gastrointestinal secretions, bronchial secretions including sputum, secretions or washings from the breast, and other associated tissue washings from a human as an aid in the detection, diagnosis, monitoring, treatment, or evaluation of neoplastic disease, including early cancer, non-invasive cancer, carcinoma in-situ, premalignancy, invasive cancer, advanced cancer, and benign neoplasm, wherein the method comprises the steps of extracting RNA from the bodily fluid, amplifying a fraction of the extracted RNA or the corresponding cDNA wherein the fraction comprises 5T4 RNA, and detecting the amplified product of 5T4 RNA or its cDNA.

The invention thereby provides the method of amplifying and detecting extracellular 5T4 RNA.

The method of the invention further provides a convenient method of detecting 5T4 RNA in cells and tissue from a human, wherein the method comprises the steps of extracting RNA from cells or tissue, amplifying a fraction of the extracted RNA or the corresponding cDNA wherein said fraction comprises 5T4 RNA, and detecting the amplified product of 5T4 RNA or its cDNA.

The invention provides for primers useful in the amplification of 5T4 mRNA or its cDNA.

The invention provides for a diagnostic kit enabling detection of 5T4 RNA, in which primers or probes used in the amplification of 5T4 RNA or its cDNA are provided. In preferred embodiments of the inventive methods, 5T4 RNA is extracted from blood, plasma, serum, or other bodily fluids using an extraction method selected from a group consisting of gelatin extraction method; silica, glass bead, or diatom extraction method; guanidinium thiocyanate acid-phenol based extraction methods; guanidinium; thiocyanate acid based extraction methods; centrifugation through a cesium chloride or similar gradient; phenol-chloroform based extraction methods; or other commercially available RNA extraction methods.

In preferred embodiments of the inventive methods, 5T4 RNA or its cDNA is amplified using an amplification method selected from a group consisting of reverse transcriptase polymerase chain reaction; ligase chain reaction; DNA signal amplification; amplifiable RNA reporters; Q-beta replication; transcription-based amplification; isothermal nucleic acid sequence based amplification; self-sustained sequence replication assays; boomerang DNA amplification; strand displacement activation; cycling probe technology; and any combination or variation thereof.

In preferred embodiments of the inventive methods, detection of the amplified 5T4 RNA or 5T4 cDNA product is performed using a detection method selected from a group consisting of gel electrophoresis; ELISA detection including modifications, including biotinylated or otherwise modified primers; hybridization using a specific, fluorescent-, radioisotope-, or chromogenically-labeled probe; Southern blot analysis; electrochemiluminescence; reverse dot blot detection; and high-performance liquid chromatography.

In a particularly preferred embodiment, 5T4 RNA is reverse transcribed to its cDNA prior to amplification.

The methods of the invention are provided as diagnostic methods for detecting 5T4 RNA in a human at risk for developing or who has developed a neoplastic, premalignant, or malignant disease consisting of cells expressing 5T4 RNA, wherein the methods comprise the steps of extracting RNA from bodily fluid, amplifying a fraction of the extracted RNA or the corresponding cDNA wherein said fraction comprises 5T4 RNA, and detecting the amplified product.

The methods of the invention thereby particularly provide diagnostic methods for identifying humans at risk for developing or who have malignancy or premalignancy of the epithelium, these malignancies including but not limited to breast, ovarian, lung, cervical, colorectal, gastric, pancreatic, bladder, endometrial, brain, kidney, and esophageal cancers, and these premalignancies and carcinoma in-situ including but not limited to cervical dysplasia, cervical intraepithelial neoplasia (CIN), bronchial dysplasia, atypical hyperplasia of the breast, ductal carcinoma in-situ, colorectal adenoma, atypical endometrial hyperplasia, and Barrett's esophagus.

The methods of the invention further provide a method to identify or select a human having 5T4 expressing malignancy or premalignancy. The invention thereby provides a method to identify, stratify, or select a human who might benefit from a 5T4-directed therapy, or from a further diagnostic test.

It is therefore the object of this invention to detect or infer the presence of 5T4-positive cancerous or precancerous cells within a human having a recognized cancer or pre-cancer, and in those not previously diagnosed, by examining the plasma or serum fraction of blood, or examining other bodily fluid, for 5T4 mRNA in either a qualitative or quantitative fashion.

An advantageous application of this invention is to therefore allow identification of humans having epithelial malignancies and premalignancies.

Another advantageous application of this invention is to allow identification of humans having 5T4 expressing neoplasms.

Another advantageous application of this invention is to allow selection of humans for 5T4 directed therapies, including biotherapies such as monoclonal antibody therapy, anti-sense therapies, and vaccines.

Another advantageous application of this invention is to provide a marker as a guide to whether adequate therapeutic effect has been achieved, or whether additional or more advanced therapy is required, and to assess prognosis in these patients.

Another advantageous application of this invention is to allow identification or analysis, either quantitatively or quantitatively, of 5T4 RNA in plasma or serum of humans during or following surgical procedures to remove premalignant or malignant lesions, and thus allow stratification of such patients as to their risk of residual cancer following the surgery, and their need for further therapy.

Another advantageous application of this invention is to allow identification or analysis of 5T4 RNA, either qualitatively or quantitatively, in the blood or other bodily fluid of a human who has completed therapy as an early indicator or relapsed cancer, impending relapse, or treatment therapy.

Specific preferred embodiments of the present invention will become evident from the following more detailed description of certain preferred embodiments and the claims.

DETAILED DESCRIPTION OF THE INVENTION

The invention relates to methods of detecting or inferring the presence of cancerous or precancerous cells which express 5T4 in a human, wherein the method consists of steps of first extracting RNA containing 5T4 RNA from bodily fluid; second, amplifying 5T4 RNA or a corresponding cDNA; and third, detecting the amplified 5T4 RNA or cDNA product. 5T4 RNA may be extracted from a bodily fluid, including but not limited to whole blood, plasma, serum, urine, effusions, ascitic fluid, saliva, cerebrospinal fluid, cervical secretions, vaginal secretions, endometrial secretions, gastrointestinal secretions, bronchial secretions including sputum, breast fluid or secretions or washings, using the methods of extraction as detailed in U.S. patent application Ser. No. 09/155,152, the entire disclosure of which has hereby been incorporated by reference. In one preferred embodiment, 5T4 is extracted from serum. It is preferred that blood be processed soon after drawing, and preferably within three hours, as to minimize any degradation of nucleic acids. In the preferred embodiment, blood is first collected by venipuncture and kept on ice and within 30 minutes of drawing the blood, serum is separated by centrifugation at 1100×g for 10 minutes at 4 degrees centigrade. Sera may then be frozen at −70 degrees centigrade until further assayed. RNA is extracted from the thawed serum following rapid thawing such as in a water bath at 37 degrees centigrade, with extraction performed using a commercial kit such as but not limited to the Perfect RNA Total RNA Isolation Kit (Five Prime-Three Prime, Inc., Boulder, Colo.), performed according to the manufacturer's directions. Other methods of RNA extraction are further provided in U.S. patent application Ser. No. 09/155,152, incorporated herein by reference.

Following the extraction of RNA from a bodily fluid, a fraction of which contains 5T4 mRNA, the 5T4 mRNA is amplified. Applicable amplifications assays are detailed in U.S. patent application Ser. No.09/155,152, as herein incorporated by reference, and include but are not limited to reverse transcriptase polymerase chain reaction (RT-PCR), ligase chain reaction, DNA signal amplification, amplifiable RNA reporters, Q-beta replication, transcription-based amplification, boomerang DNA amplification, strand displacement activation, cycling probe technology, isothermal nucleic acid sequence based amplification, and other self-sustained sequence replication assays.

In a preferred embodiment of the invention, 5T4 mRNA is reverse transcribed to its corresponding cDNA prior to amplification using methods known in the art; wherein in one such method, reverse transcription for each sample is performed in a 30 microliter volume containing 200 units of MMLV reverse transcriptase (Promega, Madison, Wis.), 1×reaction buffer, 1 mM dNTPs, 0.5 micrograms random hexamers, 25 units of RNAsin (Promnega, Madison, Wis.), and a fraction of previously extracted RNA such as 10 microliters of extracted serum RNA. The samples are then overlaid with mineral oil, and then incubated at room temperture for 10 minutes followed by 37 degrees centigrade for one hour.

Primers for amplification are selected to be specific to 5T4 nucleic acid. A preferred embodiment is amplification by polymerase chain reaction (RT-PCR), in which the preferred oligonucleotide primer sequences are as follows:

Primer 5T4-1: TCTTCGCCTCTTGTTGGC (gene location exon 2, 5T4 gene; Genbank accession #HSA012159) SEQ ID NO.:1

Primer 5T4-2: TGCAGGAAGGAACGGGA (gene location exon 1, 5T4 gene; Genbank accession #HSA012159) SEQ ID NO.:2

Primer 5T4-3: TTGGTAGGGAAGGAATTGGG (gene location exon 1, 5T4 gene; Genbank accession #HSA012159) SEQ ID NO.:3

Primer 5T4-1 and Primer 5T4-2 are particularly useful because they span the first intron.

In a preferred embodiment, 5T4 RNA is harvested from approximately 1.75 milliliter aliquots of serum or plasma, with RNA extracted using the Perfect RNA Total RNA Isolation Kit (Five Prime-Three Prime, Boulder, Col.) according to manufacturer's directions, and 10 microlitres of the extracted RNA are then reverse transcribed to its cDNA as described above. Polymerase chain reaction (RT-PCR) for the 5T4 RNA is performed using 5 microlitres of the 5T4 cDNA in a final volume of 50 microlitres. The reaction mixture contains one unit of Amplitaq Gold (Perkin Elmer Corp., Foster City, Calif.), 1×reaction buffer, 1.5 mM MgCl$_2$, 0.2 mM dNTPs, and 10 picomoles each of Primer 5T4-1 and Primer 5T4-2. The mixture is then amplified in a single-stage reaction in a thermocycler under parameters consisting of an initial 10 minute incubation at 95 degrees centigrade, followed by 45 cycles of denaturation at 94 degrees centigrade, annealing at 57 degrees centigrade, and extension at 72 degrees centigrade, each for 30 seconds in a one stage RT-PCR reaction. Detection of the amplified product may then be performed, such as by gel electrophoresis through a 4% TBE agarose gel, with staining of products with ethidium bromide for identification of the product, with the product being 101 base pair in size.

In a particularly preferred embodiment, the 5T4 cDNA is amplified by RT-PCR in a hemi-nested, two stage amplification reaction. The reaction mixture and amplification in the first stage of amplification are identical to that described above for the single stage RT-PCR reaction, except that the reaction mixture for the first stage utilizes only 1 picomole each of Primer 5T4-1 and Primer 5T4-2 (with the remainder of the reaction mixture identical to above). Thermocycling during the firs stage is performed for only 25 cycles using otherwise identical parameters to the single stage method, followed by the transferring one-tenth volume to fresh tubes, preparation of a new reaction mixture identical to above except that 10 picomoles each of Primer 5T4-1 and Primer 5T4-3 are utilized, and reamplifying for 35 additional cycles under the above thermocycling parameters. Detection of the amplified product is then performed as described, with the amplified product being 73 base pairs in size.

In preferred embodiments, detection of amplified products may similarly be performed using other detection methods, including but not limited to those selected from a group consisting of gel electrophoresis; ELISA detection including modifications, including biotinylated or otherwise modified primers; hybridization using a specific fluorescent-, radioisotope-, or chromogenically-labeled probe; Southern blot analysis; electrochemiluminescence; reverse dot blot detection; and high-performance liquid chromatography.

In one embodiment, PCR products may be further cloned, such as into the pGEM-T vector system using standard techniques. RNA may be expressed from cloned PCR products using the TnT Quick Coupled Transcription/Translation kit (Promega, Madison, Wis.) as directed by the manufacturer.

In another embodiment, restriction digestion may be performed upon the single-stage RT-PCR product with BamH I yielding two fragments of approximately 67 and 34 bp.

The methods of the invention as described above are similarly performed for the detection of 5T4 mRNA from other bodily fluids, including but not limited to whole blood, urine, effusions, ascitic fluid, saliva, cerebrospinal fluid, cervical secretions, vaginal secretions, endometrial secretions, gastrointestinal secretions, breast fluid or secretions, and bronchial secretions including sputum. The invention thereby provides the method of amplifying and detecting extracellular 5T4 mRNA.

The primers and amplification method as described herein may similarly be utilized in the amplification of 5T4 mRNA present in cells or tissue following the extraction of the intracellular RNA.

The invention thereby provides a diagnostic method for detecting 5T4 mRNA in a human at risk for developing or who has developed a neoplastic, premalignant, or, malignant disease consisting of cells expressing 5T4 mRNA The invention further provides a method of identifying humans at risk for developing, or who have cancers or premalignancies of the epithelium, including but not limited to breast, ovarian, lung, cervical, colorectal, gastric, pancreatic, bladder, endometrial, brain, kidney, and esophageal cancers, and premalignancies and carcinoma in-situ including but not limited to cervical dysplasia and cervical intraepithelial neoplasia (CIN), bronchial dysplasia, atypical hyperplasia of the breast, ductal carcinoma in-situ, colorectal adenoma, atypical endometrial hyperplasia, and Barrett's esophagus.

The diagnostic methods and advantageous applications of the invention may further be provided through a diagnostic kit, wherein the kit includes primers or probes to the 5T4 RNA or cDNA.

The inventive methods of amplification and detection of 5T4 mRNA in bodily fluids and also cells further provide significant utility in the assignment and monitoring of both non-specific therapies, and 5T4-specific therapies. The invention enables stratification and selection of patients likely to benefit from 5T4specific therapy, and provides a method of monitoring response, relapse, and prognosis. Of particular value, the invention allows the development and application of 5T4-specific therapy even when only premalignant tumors, early cancer, or occult cancers or metastases such as following resection or in minimal residual disease are present. Thus, the invention allows therapeutic intervention when tumor burden is low, immunologic function is relatively intact, and the patient is not compromised, all increasing the potential for cure.

The methods of the invention and preferred uses for the methods of the invention are more fully illustrated in the following Examples. These Examples illustrate certain

EXAMPLE 1
Detection of 5T4 mRNA in Placental and Carcinoma Tissue

5T4 glycoprotein is expressed in placental tissue, but is infrequently expressed in other normal tissue. Normal placenta was obtained within hours of delivery and stored at −80 degrees centigrade until use. Normal human tissues from other organs, consisting of normal tissue from brain, kidney, liver, skeletal muscle, spleen, and myocardium, were obtained from autopsies within 12 hours of death, snap frozen, and stored at −80 degrees centigrade until use. In addition, 8 human breast cancer specimens and 16 human lung cancer specimens were available as formalin-fixed, paraffin-embedded tissue obtained at times of biopsy or surgery.

Placental mRNA was extracted and reverse transcribed by the invention methods as described, followed by RT-PCR single stage or two-stage, hemi-nested amplification for 5T4 mRNA as described previously. The appropriate-sized 5T4 mRNA PCR product was demonstrated, indicating the expression of 5T4 mRNA in placenta. In comparison, RNA was prepared from the normal tissues obtained at autopsy. While all tissues contained amplifiable control (RARA) RNA, in none of the autopsy tissues was amplifiable 5T4 mRNA demonstrated.

To demonstrate amplification and detection of 5T4 mRNA in human cancer tissue, formalin-fixed cancer tissues were assayed. Thin sections of the fixed lung and breast cancer specimens were obtained and the RNA processed according to the method of Bianchi (1991), with the exception that harvested RNA was used directly (5 or 18 microliters of 500 total after organic extractions) rather than following ethanol precipitation for the reverse transition mixture. The extracted RNA was then amplified by RT-PCR as described using either a single-stage or two-stage PCR assay. Amplified products were detected by gel electrophoresis as described. 5T4 mRNA amplified products were detectable in 3 lung cancer specimens, and in 3 breast cancer specimens, indicating the presence of 5T4 mRNA in these specimens.

EXAMPLE 2
Detection of 5T4 mRNA In Serum From Cancer Patients

Sera was prepared from the blood of 5 patients with breast cancer and 14 patients with lung cancer in the manner described above, and then stored frozen at −70 degrees centigrade until assayed At the time of assay, the sera was thawed in a rapid manner by placing it in a water bath heated to 37 degrees centigrade. RNA was then extracted from 1.75 milliliters of sera using the Perfect RNA Total RNA Isolation Kit (Five Prime-Three Prime, Inc., Boulder, Col.) according to manufacturer's directions, as described. Ten microliters of the extracted RNA was then reverse transcribed using MMLV reverse transcriptase (Promega, Madison, Wis.) in the manner as previously described, and then amplified by PCR using the primers and amplification parameters as previously described for single stage and for two stage, hemi-nested RT-PCR amplification. All specimens were evaluated by the single stage PCR amplification, and then separately evaluated using the more sensitive two stage, hemi-nested PCR amplification reaction. Two of the 19 patients, both with lung cancer, had sera positive for 5T4 mRNA using the single-stage PCR assay, while the more sensitive hemi-nested two stage PCR assay demonstrated sera to be positive for 5T4 mRNA in 8 patients, including those of 2 breast cancer patients and 6 lung cancer patients (including both patients positive with the single-stage assay). Positive and negative controls were appropriate for all reactions.

Bibliography

1. Bianchi, A., N. Navone, and C. Conti: Detection of loss of heterozygosity in formalin-fixed paraffin-embedded tumor specimens by the polymerase chain reaction. Am. J. Path. 138: 279–284, 1991.
2. Hole, N., and Stern, P. L.: A 72 kD trophoblast glycoprotein defined by a monoclonal antibody. Br. J. Cancer 57: 239–246, 1988.
3. Hole, N., and Stern, P. L.: Isolation and characterization of 5T4, a tumour-associated antigen. Int. J. Cancer 45: 179–184, 1990.
4. Jones, H., Roberts, G., Hole, N., McDicken, I. W., and Stern, P.: Investigation of expression of 5T4 antigen in cervical cancer. Br. J. Cancer 61: 96–100, 1990.
5. King, K. W., Sheppard, F. C., Westwater, C., Stern, P. L., and Myers, K. A.: Organisation of the mouse and human 5T4 oncofoetal leucine-rich glycoprotein genes and expression in foetal and adult murine tissues. Biochimica et Biophysica Acta 1445: 257–270, 1999.
6. Mulder, W. M. C., P.L. Stern, M. J. Stukart, E. de Wmdt, R. M. J. M. Butzelaar, S. Meijer, H. J. Ader, A. M. E. Claessen, J. B. Vermorken, C. J. L. M. Meijer, J. Wagstaff R. J. Scheper, and E. Bloemena: Low intercellular adhesion molecule 1 and high 5T4 expression on tumor cells correlate with reduced disease-free survival in colo rectal carcinoma patients. Clin. Cancer Res. 3: 1923–1930, 1997.
7. Southall, P. J., G. M. Boxer, K. D. Bagshawe, N. Hole, M. Bromley, and P. L. Stern: Immunohistolgical distribution of 5T4 antigen in normal and malignant tisses. Br. J. Cancer 61: 89–95, 1990.
8. Starzynska, T., Rahi, V., and Stern, P. L.: The expression of 5T4 antigen in colorectal and gastric carcinorma. Br. J. Cancer 66: 867–869, 1992.
9. Starzynska, T., P. J. Marsh, P. F. Schofield, S. A. Roberts, K. A. Myers, and P. L. Stern: Prognostic significance of 5T4 oncofetal antigen expression in colorectal carcinoma. Br. J. Cancer 69: 899–902, 1994.

What is claimed is:

1. A method of detecting extracellular 5T4 RNA in blood plasma or serum from a human for detecting, diagnosing, monitoring, treating, or evaluating a neoplastic disease comprising cells that express 5T4 RNA, the method comprising the steps of:
   (a) extracting heterogeneous human extracellular RNA from blood plasma or serum;
   (b) amplifying a portion of the extracted RNA or the corresponding cDNA to produce an amplified DNA fragment, wherein said portion comprises 5T4 RNA, and wherein amplification is performed in either a qualitative or quantitative fashion using primers or probes specific for 5T4 RNA or corresponding cDNA; and
   (c) detecting the amplified fragment produced from 5T4 RNA or corresponding cDNA.

2. The method of claim 1, wherein the amplification in step (b) is performed by an amplification method that is reverse transcriptase polymerase chain reaction, ligase chain reaction, branched DNA signal amplification, amplifiable RNA reporters, Q-beta replication, transcription-based amplification, isothermal nucleic acid sequence-based amplification, self-sustained sequence replication assay, boomerang DNA amplification, strand displacement activation or cycling probe technology.

3. The method of claim 1, wherein detection of amplified product in step (c) is performed using a detection method that is gel electrophoresis, ELISA detection using biotinylated or other modified primers, labeled fluorescent or chromagenic probes, Southern blot analysis, electroluminescence, reverse blot detection, or high-preformance liquid chromatography.

4. The method of claim 1, wherein the human is a human at risk for a malignancy or premalignancy wherein the method comprises a screening method for malignancy or premalignancy, wherein 5T4 is expressed in said malignancy or premalignancy and wherein detection of 5T4 RNA in the plasma or serum fraction of blood of said human indicates that malignant or premalignant cells are present in the body of said human.

5. The method of claim 4, wherein the malignancy is breast cancer or lung cancer.

6. A method according to claim 1, wherein the human is a human with cancer who is selected for a 5T4 directed therapy when 5T4 RNA is detected in the human's plasma or serum.

7. A method according to claim 1, further comprising the step of performing a further diagnostic test when 5T4 RNA is detected in plasma or serum of a human.

8. A method according to claim 1, wherein the human is a human with cancer to whom anticancer therapy is administered, and wherein detection of 5T4 RNA is used to monitor a response to therapy.

9. A method of detecting extracellular 5T4 RNA in a bodily fluid from a human for detecting, diagnosing, monitoring, treating, or evaluating a neoplastic disease comprising cells that express 5T4 RNA, the method comprising the steps of:
   (a) extracting heterogeneous human extracellular RNA from a bodily fluid;
   (b) amplifying a portion of the extracted RNA or corresponding cDNA to produce an amplified DNA fragment, wherein said portion comprises 5T4 RNA, and wherein amplification is performed in either a qualitative or quantitative fashion using primers or probes specific for the 5T4 RNA or corresponding cDNA; and
   (c) detecting the amplified fragment produced from 5T4 RNA or corresponding cDNA product.

10. The method of claim 9, wherein the amplification in step (b) is performed by an amplification method that is reverse transcriptase polymerase chain reaction, ligase chain reaction, branched DNA signal amplification, amplifiable RNA reporters, Q-beta replication, transcription-based amplification, isothermal nucleic acid sequence-based amplification, self-sustained sequence replication assay, boomerang DNA amplification, strand displacement activation or cycling probe technology.

11. The method of claim 9, wherein detection of amplified DNA fragment produced in step (c) is performed using a detection method that is gel electrophoresis, capillary electrophoresis, ELISA detection including using biotinylated or other modified primers, labeled fluorescent or chromagenic probes, laser-induced fluorescence, Southern blot analysis, Northern blot analysis, electroluminescence, reverse blot detection, or high-performance liquid.

12. The method of claim 9, wherein the human is a human at risk for a malignancy or premalignancy wherein the method comprises a screening method for malignancy or premalignancy, wherein 5T4 is expressed in said malignancy or premalignancy and wherein detection of 5T4 RNA in the plasma or serum fraction of blood of said human indicates that malignant or premalignant cells are present in the body of said human.

13. The method of claim 12, wherein the malignancy is breast cancer or lung cancer.

14. A method according to claim 9, wherein the human is a human with cancer who is selected for a 5T4 directed therapy when 5T4 RNA is detected in the human's plasma or serum.

15. A method according to claim 9, further comprising the step of performing a further diagnostic test when 5T4 RNA is detected in plasma or serum of a human.

16. A method according to claim 9, wherein the human is a human with cancer to whom anticancer therapy is administered, and wherein detection of 5T4 RNA is used to monitor a response to therapy.

17. A method of identifying a human having 5T4 expressing cells or tissue, the method comprising the steps of:
  a) extracting heterogeneous human extracellular RNA from a bodily fluid of the human;
  b) amplifying a portion of the extracted extracellular RNA or the corresponding cDNA to produce an amplified DNA fragment, wherein said portion comprises 5T4 RNA, and wherein amplification is performed in either a qualitative or quantitative fashion using primers or probes specific for the 5T4 RNA or corresponding cDNA; and
  c) detecting the amplified DNA fragment produced from 5T4 RNA or corresponding cDNA product, whereby detection thereby identifies a human having 5T4 RNA expressing cells or tissue.

18. The method of claim 17, wherein the 5T4 expressing cells or tissue are those of a malignancy, or premalignancy or carcinoma in-situ.

19. The method of claim 18, wherein the malignancy is breast cancer or lung cancer.

20. The method of claim 17, wherein the human is one at risk for developing a malignancy or premalignancy.

21. The method of claim 17, wherein the human is known to have a malignancy or premalignancy or carcinoma in-situ.

22. A method for selecting a human with cancer for a 5T4 directed therapy, the method comprising the steps of:
  a) extracting heterogeneous human extracellular RNA from cells or tissue from the human's cancer;
  b) amplifying a portion of the extracted extracellular RNA or corresponding cDNA to produce an amplified DNA fragment, wherein said portion comprises 5T4 RNA, and wherein amplification is performed in either a qualitative or quantitative fashion using primers or probes specific for the tumor-derived or tumor-associated RNA or corresponding cDNA; and
  c) detecting the amplified DNA product produced from 5T4 RNA or corresponding cDNA product, whereby detection of the amplified 5T4 RNA or cDNA product selects the human with cancer for a 5T4 directed therapy.

23. A kit comprising primers or probes for amplifying 5T4 RNA or cDNA prepared therefrom, wherein the primers comprise at least one of the following sequences:
  a) TCTTCGCCTCTTGTTGGC (SEQ ID No.: 1)
  b) TGCAGGAAGGAACGGGA (SEQ ID No. :2), or
  c) TTGGTAGGGAAGGAATTGGG (SEQ ID No.: 3).

* * * * *

UNITED STATES PATENT AND TRADEMARK OFFICE
CERTIFICATE OF CORRECTION

PATENT NO. : 6,794,135 B1
DATED : September 21, 2004
INVENTOR(S) : Michael S. Kopreski and Christopher D. Gocke It is certified that error appears in the above-identified patent and that said Letters Patent is hereby corrected as shown below:

Column 12,
Lines 21-22, delete "the tumor-derived or tumor-associated" and insert -- 5T4 -- in its place.

Signed and Sealed this

Twenty-first Day of December, 2004

JON W. DUDAS
*Director of the United States Patent and Trademark Office*